United States Patent [19]

Cameto et al.

[11] Patent Number: 4,506,511

[45] Date of Patent: Mar. 26, 1985

[54] THERMOELECTRIC AIR COOLER FOR THERAPEUTIC TENTS

[75] Inventors: L. Robert Cameto, Oakland, Calif.; Robert M. Jepson, Lake Villa, Ill.

[73] Assignee: Misto₂Gen Equipment Corporation, Lancaster, Pa.

[21] Appl. No.: 541,408

[22] Filed: Oct. 13, 1983

[51] Int. Cl.³ .............................................. F25B 21/02
[52] U.S. Cl. .................................................... 62/3
[58] Field of Search ............................................ 62/3

[56] References Cited

U.S. PATENT DOCUMENTS 3,212,275 10/1965 Tillman ..................................... 62/3
3,283,520 11/1966 Donohue et al. ......................... 62/3
3,839,876 10/1974 Privas ...................................... 62/3

FOREIGN PATENT DOCUMENTS 308409 2/1963 France .
1353485 6/1964 France .

Primary Examiner—Lloyd L. King
Attorney, Agent, or Firm—Townsend and Townsend

[57] ABSTRACT

A thermoelectric cooler is used to cool the air within a therapeutic tent and includes a housing supported by a stand. Thermoelectric modules are sandwiched between hot and cold spacing blocks. A cold spacing block is sized to fit within a complementary opening in the housing. Air from the tent is blown past a finned cooling heat exchanger, secured to the cold spacing block within a cool air enclosure, to cool the air and return it to the tent. The cooling heat exchanger and cool air enclosure defining the cool air path are may be removed for cleaning and sterilization after use. Potentially contaminated air from the tent never touches the main housing or the various components housed within the main housing.

18 Claims, 6 Drawing Figures

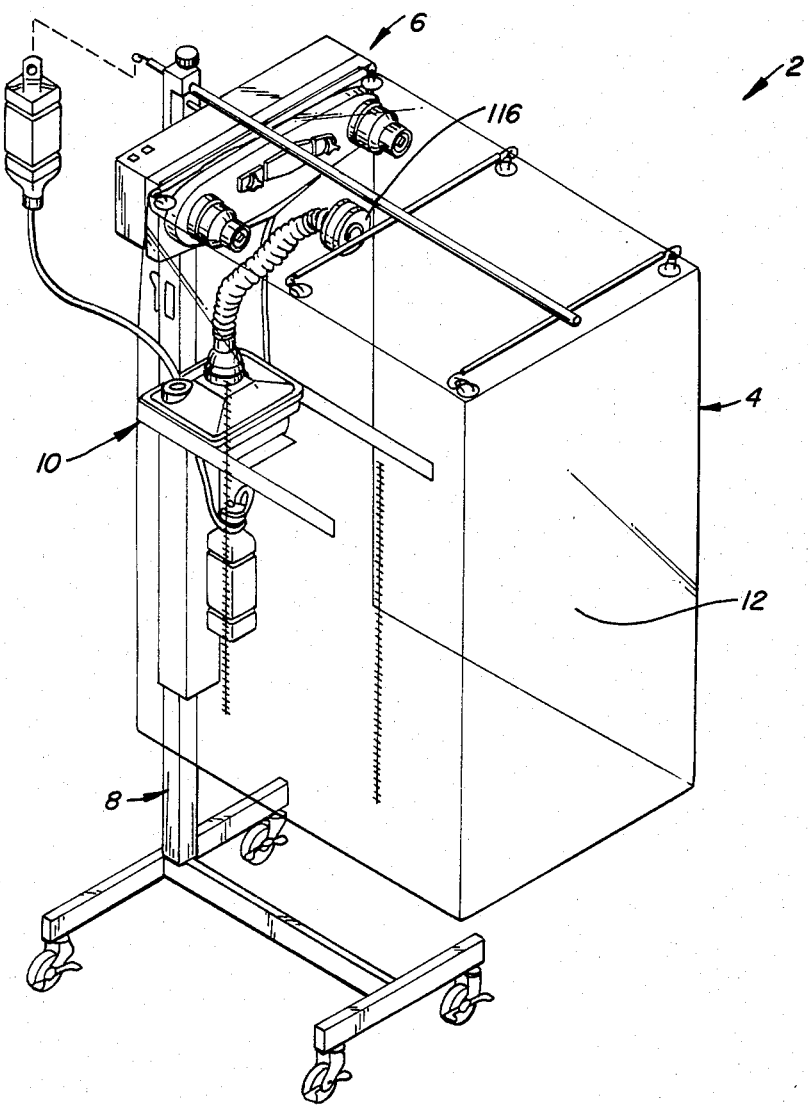
FIG._1.

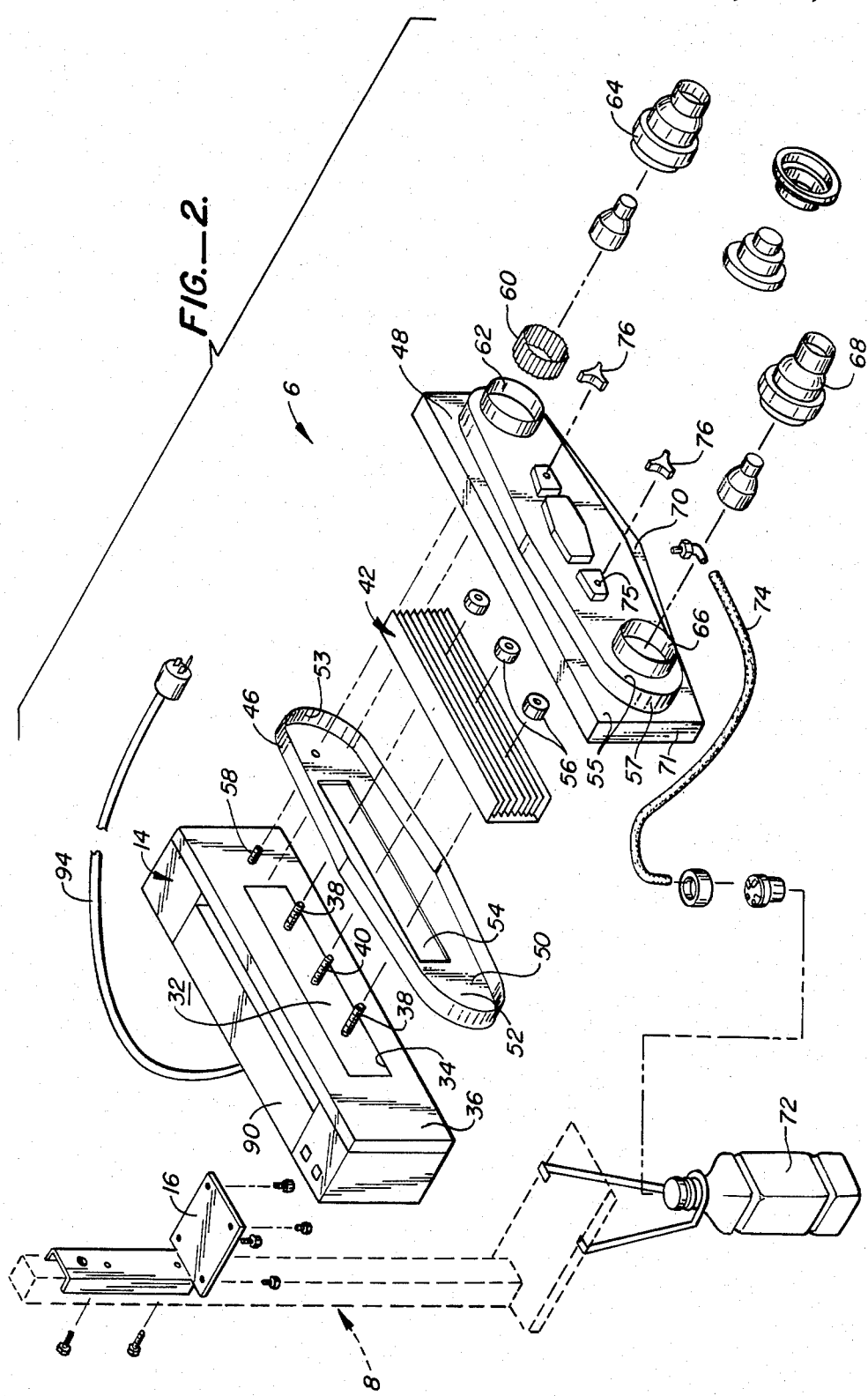

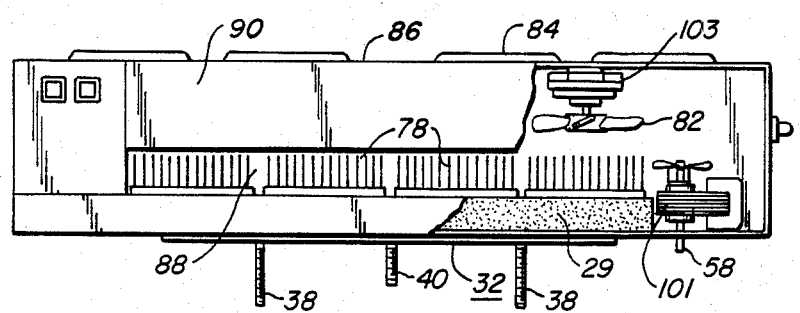
FIG._3.
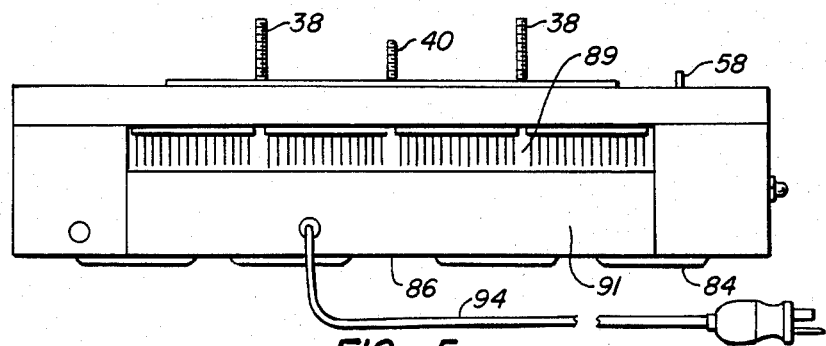
FIG._5.
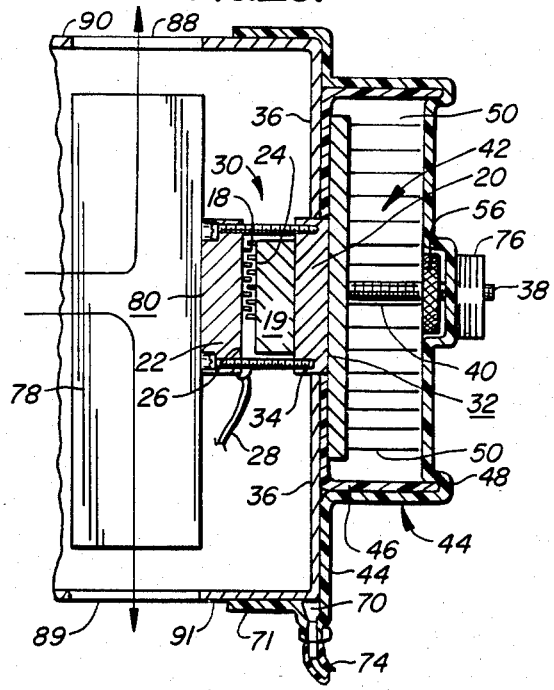
FIG._4.

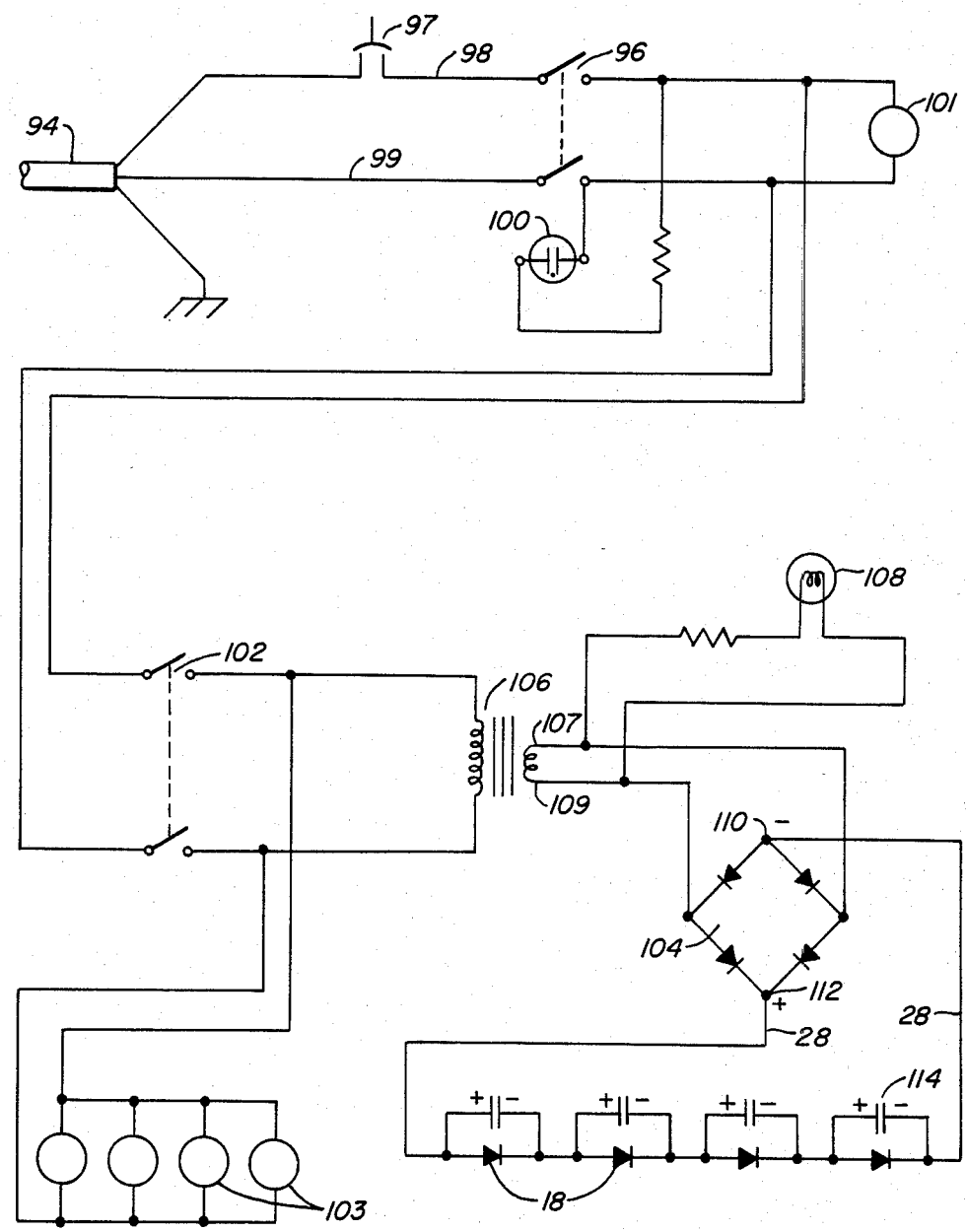
FIG._6.

THERMOELECTRIC AIR COOLER FOR THERAPEUTIC TENTS

BACKGROUND OF THE INVENTION

Therapeutic tents are commonly used to surround a bed patient to provide the patient with a conditioned air environment. In particular, children and adults in respiratory distress are often placed within transparent plastic tents for aerosol therapy. This is a more convenient means of aerosol delivery than using closed respirators and other inhalation therapy devices. Although the mist and expanding gas (often oxygen enriched) has a cooling effect, body heat of the patient soon makes the environment uncomfortably warm and humid, thus impairing the value of the therapy. It is therefore desirable to maintain the environment at a comfortable temperature and humidity while delivering aerosol for indefinite periods of time.

To condition the air, ice and ice filled heat exchangers, with and without recirculating fans, have often been used. These have several disadvantages, the most obvious being the need for replenishing the ice and removing the water.

Conventional refrigeration systems of the type including a compressor, a condensor, a heat exchanger, and a fan to move the air have been used instead of the ice cooling systems. An example of such an compressor type cooling apparatus is distributed by Ohio Medical Products of Madison, Wis. Although in many ways an improvement over ice cooling systems, a conventional compressor refrigeration system requires the usual maintenance and generates a fair amount of noise. They are also bulky, relatively expensive and difficult to clean between uses. To eliminate the noise from the fan, one version of a compressor refrigeration system uses a large condensor mounted within the tent. However, this system is bulky, difficult to set up, difficult to clean and is a relative inefficient heat exchanger.

U.S. Pat. No. 3,283,502 to Donohue discloses a thermoelectric cooler for oxygen tents. Although this design eliminates some of the problems associated with compressor refrigeration systems, the unit is still large and bulky. It also appears that the unit would be quite difficult to clean thoroughly between uses because the paths traversed by the cool air and its general physical construction.

What has been missing in the prior art is a small, lightweight, quiet, easy to clean and sterilize heat exchanger for cooling the air within a therapeutic tent.

SUMMARY OF THE INVENTION

The present invention is directed to a thermoelectric air cooler, a part of a therapeutic misting or oxygen tent, used to cool the air within the tent enclosure. The thermoelectric air cooler includes a main housing supported by a stand. Within the main housing a number of thermoelectric modules are sandwiched between hot and cold spacing blocks. One of the cold spacing blocks is a unitary structure sized to fit within a complementary opening within the front face of the main housing. The outer, external surface of the cold spacing block preferably extends a small distance in front of the front face of the main housing.

A finned cooling heat exchanger is secured to the cold spacing block. A cool air enclosure defines a cool air path from a conditioned air intake, past the cooling heat exchanger and to a conditioned air exhaust, such intake and exhaust connected to the interior of the tent enclosure. The cool air enclosure includes a rear cover having a central opening sized to fit around the outer surface of the cold spacing block and between the main housing and the cooling heat exchanger.

The cooling heat exchanger and cool air enclosure are removably secured to the main housing so that they may be removed for cleaning and sterilization after use. However, since potentially contaminated air from the tent enclosure never touches the main housing or the various components housed within the main housing, cleaning and sterilization is limited to a relatively few, easily removed components.

Finned hot air heat exchangers are mounted to the hot spacing blocks in the main housing. Fans are used to draw ambient air from outside the main enclosure, across the fins of the hot air heat exchangers and out vents in the enclosure to provide the necessary cooling to the thermoelectric module.

A primary advantage of the present invention is that the parts of the cooler coming in contact with air respirated by the patient can be easily removed for cleaning and sterilization. Since the bulk of the cooler is isolated from the cool air path containing the respirated, potentially contaminated air, that portion need not be sterilized between uses. The air cooler of the invention is also compact for ease of handling and quiet for increased patient comfort.

The cool air path is generally straight to minimize the pressure drop. This reduces the fan size necessary to force the air pass the cooling heat exchanger. Noise generation and power consumed are thereby minimized.

Other features and advantages of the present invention will appear from the following description in which the preferred embodiment has been set forth in detail in conjunction with the accompanying drawings.

BRIEF DESCRIPTION OF THE DRAWINGS

FIG. 1 is an overall perspective view of a therapeutic tent including an air cooler made according to the present invention.

FIG. 2 is an exploded isometric view of the removable components of the cooler of FIG. 1.

FIG. 3 is a top view of the main housing of FIG. 1 with parts broken away for clarity.

FIG. 4 is an enlarged sectional view of the heat exchangers, spacing blocks, thermoelectric module and cool air enclosure with insulation removed for clarity.

FIG. 5 is a bottom view of the cooler of FIG. 1.

FIG. 6 is a schematic diagram of the electrical components of the cooler of FIG. 1.

DETAILED DESCRIPTION OF THE PREFERRED EMBODIMENT

Turning to FIGS. 1 and 2, a therapeutic tent 2 includes a tent enclosure 4 and a thermoelectric air cooler 6, both supported by a stand 8. Tent enclosure 4 is typically made of clear plastic and is sized to surround a patient in a bed. Stand 8 is adapted to be easily wheeled to the patient's bedside. Also shown in FIG. 1 is a misting assembly 10 for supplying an aerosol mist to the conditioned air region 12 within tent enclosure 4. However, cooler 6 can be used with or without misting assembly 10 so assembly 10 will not be described further.

Cooler 6 includes a main housing 14 mounted to stand 8 by a bracket 16. Turning now also to FIGS. 3 and 4, four thermoelectric modules 18 are sandwiched between four cold spacing blocks 19, a unitary cold spacing block 20 and four hot spacing blocks 22. Modules 18 are of a type commercially available, such as those sold by Thermoelectric Industries of Lake Villa, Ill. Cold spacing blocks 19 are mounted to the cold junction surfaces 24 of modules 18 while hot spacing blocks 22 are mounted to the hot junction surfaces 26 of modules 18. Blocks 19 are sandwiched between cold junction surfaces 24 and unitary cold spacing block 20. Passage of current from conductors 28 to modules 18 cools junction surfaces 24 and heats junction surfaces 26, and thus cold spacing blocks 19 and 20 and hot spacing blocks 22, in the well-known manner. The region surrounding the spacing blocks is filled with a foam insulation 29 for increased thermal efficiency.

Together hot spacing blocks 22, thermoelectric modules 18, cold spacing blocks 19 and unitary cold spacing block 20 comprise a heating and cooling subassembly 30. Sub-assembly 30 is mounted within housing 14 so that the outer surface 32 of unitary cold spacing block 20 passes through a complementary opening 34, indicated in FIG. 2, formed within front face 36 of housing 14. Threaded mounting posts 38, 40 extend from surface 32 of cold spacing block 20 and are used to mount finned cooling heat exchanger 42 against surface 32.

Referring to FIGS. 2 and 4, a cool air enclosure 44, including a rear cover 46 and a front cover 48, defines a cool air region 50 within enclosure 44. Region 50 is also bounded by exchanger 42. Rear cover 46 is in the shape of an elongate pan with a bottom 52 and lip 53 and has a central opening 54 sized to surround surface 32 of spacing block 20 which extends partially through opening 34. Front cover 48 includes a stepped outer surface 55 coupled by an intermediate lip 57 configured for complementary engagement around lip 53. Knurled nuts 56 are used to secure cooling heat exchanger 42 to main housing 14. Exchanger 42 is larger than surface 32 so exchanger 42 also secures rear cover 46 to main housing 14.

A cooling fan drive shaft 58 extends from main housing 14 and passes through an opening in rear cover 46. Shaft 58 drives a recirculating fan 60 mounted thereto. Fan 60 is located adjacent a conditioned air intake 62 formed within front cover 48. Air from region 12 within tent enclosure 4 is drawn through an air passageway 64, through intake 62 and past recirculating fan 60 where it is blown across the fins of cooling heat exchanger 42. Thereafter the air, cooled as it passes heat exchanger 42, leaves region 50 and passes out an exhaust port 66, through an exhaust passageway 68 and back into region 12. As the air is cooled in region 50, moisture is condensed and collects at a low point 70 in a peripheral lip 71 of front cover 48. The condensate is allowed to drain into a bottle 72 through a tube 74 connected to low point 70.

Mounting posts 38, longer than mounting post 40, extend through appropriately placed holes 75 in front cover 48. A pair of threaded caps 76 are threaded onto posts 38 to secure front cover 48 against rear cover 46 and housing 14. Caps 76 and nuts 56 can be removed by hand to allow front cover 48, cooling fan 60, exchanger 42, and rear cover 46 to be easily removed from housing 14 to allow these components to be sterilized. The only other pieces extending into cool air region 50, and thus requiring sterilization, are mounting posts 38, 40 and shaft 58. These components can all be easily sterilized without dismantling housing 14.

Referring to FIGS. 3, 4 and 5, the heat produced at hot junction surface 26 and carried away by hot spacing blocks 22 is dissipated by several finned heat exchangers 78 mounted to surfaces 80 of blocks 22. Four cooling fans 82 are mounted within main housing 14, one opposite each heat exchanger 78. Fans 82 draw ambient air into housing 14 through openings 84 in the rear panel 86 of the housing. Such air is blown across heat exchangers 78 and exits housing 14 through openings 88, 89 in the top and bottom panels 90, 91 of housing 14 to draw heat away and thus cool heat exchangers 78.

Turning now to FIG. 6, a schematic circuit diagram of the electrical components of the invention is shown. Power is supplied to main housing 14 by power cord 94. A double-pole, double-throw recirculate switch 96 is mounted across hot lines 98, 99 for supplying power through a circuit breaker switch 97 to an indicator light 100, the motor 101 of recirculating fan 60 and a recirculate and cool switch 102. Closing both switches 96 and 102 provides power to the motors 103 of fans 82 and also to a rectifier bridge 104 through a transformer 106 via lines 107, 109. A cooling indicator light 108 also connected to lines 107, 109 is therefore illuminated when in the cooling mode. Thermoelectric modules 18 are connected in series to the output terminals 110, 112 of bridge 104. Filter capacitors 114 are placed across modules 18 to enhance their performance.

In use, therapeutic tent 2 is placed adjacent a patient's bed, not shown, so that tent enclosure 4 surrounds the patient. If misting is desired, misting assembly 10 is activated to deliver the mist into conditioned air region 12 through a misting port 116 in tent enclosure 4. To keep the air within region 12 at a comfortable temperature, thermoelectric air cooler 6 is fluidly coupled to region 12 by extending the distal ends of exhaust passageways 64, 68 through complementary openings in tent enclosure 4.

Air within region 12 is recirculated through region 50 by closing recirculate switch 96. If it is desired to both cool and recirculate the air within region 12, switches 96 and 102 are both closed actuating recirculating fan 60, cooling fans 82 and thermoelectric devices 18. Air is drawn into cool air region 50 by fan 60 and is forced through intake port 62, past cooling heat exchanger 42 and out exhaust port 60 where it is reintroduced into region 12 through exhaust passageway 68. Moisture which condenses during cooling is collected at low point 70 and directed to bottle 72.

Modification and variation can be made to the disclosed embodiment without departing from the subject of the invention as defined in the following claims. For example, various temperature sensors can be used to automatically control the current through thermoelectric devices 18 and thus the amount of cooling supplied by cooler 6.

We claim:

1. A thermoelectric air cooler for use in combination with a therapeutic tent of the type including a tent enclosure defining a conditioned air region for creating a controlled ambient atmosphere for a patient, said thermoelectric air cooler comprising:

a main housing;

a thermoelectric module mounted within the housing and having hot and cold junction surfaces;

a generally planar cold surface at an external wall of said main housing thermally coupled to said cold junction surface;

a cooling heat exchanger thermally coupled to said cold surface;

a cool air enclosure having a conditioned air intake and a conditioned air exhaust and defining a cool air path from said conditioned air intake, past said cooling heat exchanger and to said conditioned air exhaust, said cool air enclosure and said cooling heat exchanger arranged and adapted so said cool air path is physically isolated from and external to said main housing;

passageways fluidly connecting the conditioned air region with said conditioned air intake and exhaust;

means for removably mounting said cooling heat exchanger and said cool air enclosure to said main housing so said cooling heat exchanger and said cool air enclosure can be removed and cleaned separate from said main housing thereby aiding sterilization of the components of the air cooler contacting air from said conditioned air region;

a fan adapted for forcing air along said cool air path so air from the conditioned air region is cooled as it passes said cooling heat exchanger;

a hot air heat exchanger thermally coupled to said hot junction surface; and means for removing heat from said hot air heat exchanger.

2. The air cooler of claim 1 including a plurality of thermoelectric modules and a common cold spacing block thermally coupled to said cold junction surfaces of said modules.

3. The air cooler of claim 2 further comprising a plurality of intermediate cold spacing blocks sandwiched between said common cold spacing block and said cold junction surfaces.

4. The air cooler of claim 2 wherein said common cold spacing block includes said cold surface, and said housing includes a first opening sized so said cold surface passes through said first opening.

5. The air cooler of claim 1 wherein said cold surface is generally parallel to said external wall of said main housing.

6. The air cooler of claim 1 wherein said cooling heat exchanger includes a plurality of fins.

7. The air cooler of claim 1 wherein said cool air enclosure includes a rear cover, a portion of which is positioned between said cooling heat exchanger and said external wall, and a front cover adapted to matingly engage said rear cover with said cooling heat exchanger therebetween.

8. The air cooler of claim 7 wherein said rear cover includes an outwardly extending peripheral lip for mating engagement with a complementarily shaped inwardly extending lip on said front cover.

9. The air cooler of claim 8 wherein said inwardly extending lip surrounds said outwardly extending lip.

10. The air cooler of claim 9 wherein said outer cover includes a stepped outer surface connected by said inwardly extending lip and circumscribed by a peripheral lip closely surrounding said first surface of said main housing.

11. The air cooler of claim 8 wherein said cool air enclosure includes a drain at a low point along said lips.

12. The air cooler of claim 8 wherein said inwardly extending lip surrounds said outwardly extending lip and includes said drain.

13. The air cooler of claim 1 wherein said cool air path is generally straight between said conditioned air intake and exhaust.

14. The air cooler of claim 1 wherein said hot air heat exchanger includes a finned heat exchanger located within said main housing, said main housing having openings formed therein to allow ambient air to enter and exit said main housing to remove heat from said finned heat exchanger, and wherein said heat removing means includes a fan, mounted within said main housing, for blowing air past said finned heat exchanger.

15. The air cooler of claim 1 further comprising a hot spacing block mounted to said hot junction surface of said thermoelectric module.

16. The air cooler of claim 1 wherein said hot air heat exchanger includes a finned heat exchanger and said hot air removing means includes a fan for forcing ambient air past said finned heat exchanger.

17. A thermoelectric air cooler for use in combination with a therapeutic tent of the type including a tent enclosure defining a conditioned air region for creating a controlled ambient atmosphere for a patient, said thermoelectric air cooler comprising:

a main housing including a first opening;

a plurality of thermoelectric modules mounted within the housing and having hot and cold junction surfaces;

a common cold spacing block;

a plurality of intermediate cold spacing blocks sandwiched between said common cold spacing block and said cold junction surfaces, said common cold spacing block being configured so an outer surface thereof passes through said first opening and lies generally aligned with said external wall;

a cooling heat exchanger;

a cool air enclosure having a conditioned air intake and a conditioned air exhaust and defining a cool air region from said conditioned air intake, past said cooling heat exchanger and to said conditioned air exhaust, said cool air enclosure and said cooling heat exchanger arranged and adapted so said cool air region is isolated from said main housing;

passageways fluidly connecting the conditioned air region with said conditioned air intake and exhaust;

means for removably mounting said cooling heat exchanger and said cool air enclosure to an external surface of said main housing so components of the thermoelectric air cooler which contact the conditioned air can be removed and cleaned separate from said main housing thereby aiding sterilization of said components;

a fan adapted for forcing air along said cool air path so air from the conditioned air region is cooled as it passes said cooling heat exchanger;

a hot air heat exchanger mounted to said hot junction surface; and fan means for blowing air past said hot air heat exchanger to remove heat from said hot heat exchanger.

18. The air cooler of claim 17 wherein said cool air enclosure includes a rear cover, a portion of which is positioned between said cooling heat exchanger and said main housing, and a front cover adapted to overlie said rear cover with said cooling heat exchanger therebetween.

* * * * *